(12) United States Patent
Juhl

(10) Patent No.: US 9,606,050 B2
(45) Date of Patent: Mar. 28, 2017

(54) METHOD FOR COMPENSATING AMPLITUDE DRIFT IN A SPECTROMETER AND SPECTROMETER PERFORMING SAID METHOD

(75) Inventor: Henrik Vilstrup Juhl, Roskilde (DK)

(73) Assignee: FOSS ANALYTICAL A/B, Hilleroed (DK)

(*) Notice: Subject to any disclaimer, the term of this patent is extended or adjusted under 35 U.S.C. 154(b) by 553 days.

(21) Appl. No.: 14/127,424

(22) PCT Filed: Aug. 19, 2011

(86) PCT No.: PCT/EP2011/064302
§ 371 (c)(1),
(2), (4) Date: Dec. 18, 2013

(87) PCT Pub. No.: WO2013/026466
PCT Pub. Date: Feb. 28, 2013

(65) Prior Publication Data
US 2014/0114601 A1   Apr. 24, 2014

(51) Int. Cl.
*G01C 19/00* (2013.01)
*G01N 21/25* (2006.01)
*G01J 3/28* (2006.01)
*G01J 3/45* (2006.01)

(52) U.S. Cl.
CPC .............. *G01N 21/255* (2013.01); *G01J 3/28* (2013.01); *G01J 3/45* (2013.01)

(58) Field of Classification Search
CPC ............ G01N 21/255; G01J 3/28; G01J 3/45
USPC .......................................................... 702/104
See application file for complete search history.

(56) References Cited

U.S. PATENT DOCUMENTS

| 5,790,250 A | * | 8/1998 | Wang | G01J 3/453 356/451 |
| 5,850,623 A | * | 12/1998 | Carman, Jr. | G01J 3/28 250/252.1 |
| 5,933,792 A | | 8/1999 | Andersen et al. | |
| 6,297,505 B1 | | 10/2001 | Frandsen et al. | |

(Continued)

OTHER PUBLICATIONS

International Search Report PCT/ISA/210 for PCT/EP2011/064302 dated May 25, 2012.

(Continued)

*Primary Examiner* — Mischita Henson
*Assistant Examiner* — Stephanie Bloss
(74) *Attorney, Agent, or Firm* — Harness, Dickey & Pierce, PLC

(57) ABSTRACT

Compensating for amplitude drift in a spectrometer may include making successive performances of a standardization process to generate, at each performance, a mathematical transform to compensate for amplitude drift for application by an arithmetic unit to a spectrum obtained by the spectrometer in an interval between the performances. The compensating may include modifying the mathematical transform with a function dependent on spectral data from a zero material measured in association with the standardization process and the single beam zero spectrum measured in an interval between performances. The compensating may include applying the modified mathematical transform to a spectrum from an unknown sample.

7 Claims, 1 Drawing Sheet

(56) References Cited

U.S. PATENT DOCUMENTS

| | | | | |
|---|---|---|---|---|
| 6,610,982 B2* | 8/2003 | Hoult | ........................ | G01J 3/28 |
| | | | | 250/339.09 |
| 2003/0189709 A1* | 10/2003 | Maynard | ................. | G01J 3/453 |
| | | | | 356/451 |
| 2008/0290279 A1* | 11/2008 | Juhl | ......................... | G01J 3/28 |
| | | | | 250/339.08 |
| 2010/0282958 A1 | 11/2010 | Will et al. | | |
| 2013/0228690 A1* | 9/2013 | Juhl | ................... | G01N 21/3577 |
| | | | | 250/341.6 |
| 2014/0336972 A1* | 11/2014 | Juhl | ......................... | G01J 3/45 |
| | | | | 702/104 |

OTHER PUBLICATIONS

Written Opinion PCT/ISA/237 for PCT/EP2011/064302 dated May 25, 2012.

\* cited by examiner

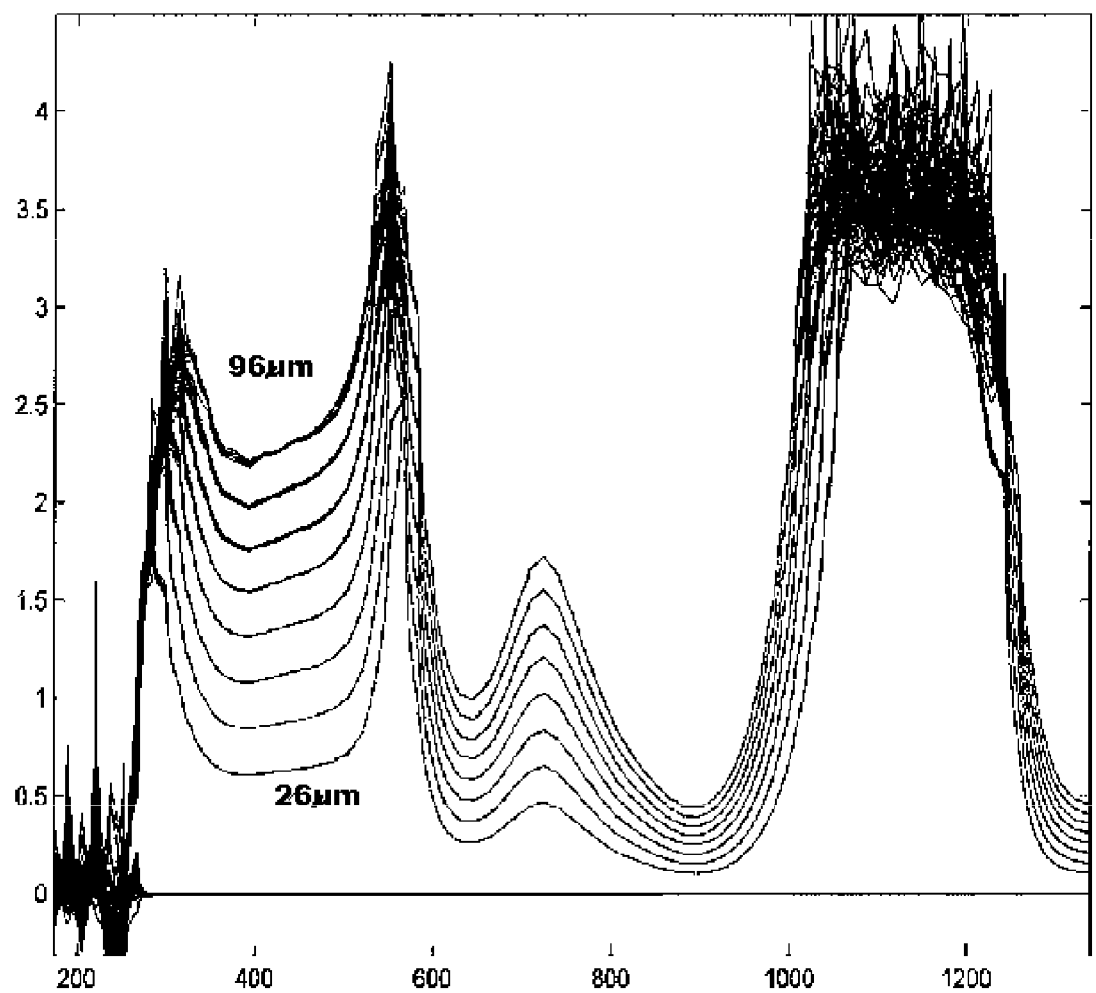

METHOD FOR COMPENSATING AMPLITUDE DRIFT IN A SPECTROMETER AND SPECTROMETER PERFORMING SAID METHOD

CROSS-REFERENCE TO RELATED APPLICATIONS

This application is a national phase under 35 U.S.C. §371 of PCT International Application No. PCT/EP2011/064302 which has an International filing date of Aug. 19, 2011.

BACKGROUND

Technical Field

The present invention relates to a method of compensating for amplitude drift in a spectrometer generating spectral data from unknown samples and in particular to the compensation for amplitude drift due to changes in an optical path length through a sample holder.

Related Art

In typical spectrometers for generating spectral data from unknown samples, a light emitter and a light detector are configured to define a light-path into which the sample in question is positioned in order to have the sample interact with the light. Typically a sample holder, such as a sample cuvette for liquid samples, is used for holding samples within the light-path in a repeatable manner. The sample holder has an internal sample receiving volume and is provided with surfaces, usually opposing surfaces, at least portions of which are transparent to the light being interacted with the sample. The separation between these transparent portions delimits an optical path-length through the sample.

BRIEF DESCRIPTION OF THE DRAWINGS

FIG. 1 illustrates an absorbance spectrum at different path lengths through a cuvette, for path lengths from 26 μm to 96 μm inclusive in 10 μm steps, according to at least one example embodiment.

DETAILED DESCRIPTION

In the present context, it is preferred that the spectrometer generates a continuous spectrum of the unknown sample. This type of spectrometer may employ a stationary or movable grating and stationary or movable detector or detectors or any other suitable means. The presently preferred spectrometer is, however, one which includes a Fourier Transform (FT) interferometer.

The usual manner of obtaining the necessary spectral data in any spectrometer is by generating a transmittance (or absorbance) spectrum of the sample. To do this a so-called single beam spectrum ($SB_S$) is obtained which comprises spectral data relating to both the sample and the spectrometer. In order to isolate the spectral data related to the sample, a similar single beam spectrum ($SB_Z$) is typically measured on a so-called zero-material, such as water (if, for example, the sample to be measures is a liquid) or air (if, for example, the sample to be measured is a solid), wherein the same effects related to the spectrometer are included but wherein effects due to the sample are not present. The zero-material spectrum is then employed to provide a wavelength dependent zero level across the spectral region within which the spectral data is collected.

The single beam spectrum of the sample ($SB_S$) is subsequently divided by the single beam spectrum of the zero-material ($SB_Z$) at the same wavelengths throughout the respective spectra in order to obtain a so-called dual beam spectrum of the sample ($DB_S$) which is essentially the transmittance spectrum of the sample relative to the zero-material and relates virtually only to the transmission properties of the sample. As is well known, taking the negative $\log_{10}$ of this provides the absorbance spectrum for the sample. These operations are usually performed in an arithmetic unit which is associated with the spectrometer and which is provided either integral with or separate but in operable connection to the spectrometer, for example in the form of a suitably programmed personal computer.

Over time the output of the spectrometer tends to vary. This variation may be described as a frequency drift as a result of which the same wavelength may not be represented identically by two otherwise similar spectrometers or by two runs of the same spectrometer, and an intensity drift as a result of which different intensities are measured at the same wavelengths for the same sample in two otherwise similar spectrometers or at two runs of the same spectrometer.

In order to take into account the potential drift of the spectrometer, it is preferred that the spectrometer is periodically standardised in a manner well known in the art, such as according to the method disclosed in U.S. Pat. No. 5,933,792, the contents of which is incorporated herein by reference. During this process a standardisation sample or samples is/are introduced and handled in the spectrometer in the same manner as unknown samples to be measured in order to obtain a single beam spectrum ($SB_{SS}$) of the standardisation sample(s). In this manner, no additional optical elements need be introduced in the light path the effect of which may introduce an additional effect, which may be compensated for, but which is not present when performing measurements on normal samples. Each standardisation sample has a chemical composition selected to produce known characteristic patterns in the associated single beam spectrum obtained by the spectrometer.

As not only the frequency axis but also the absorbance axis of the spectral data generated by the spectrometer is preferably standardised, it is typically required to also have information from the standardisation sample(s) relating to well defined absorbance values at well defined frequencies. Thus, it is preferred that the concentration(s) of the components of the standardisation sample(s) is/are kept within such tolerances that any error on the amplitude axis of the spectrum ascribable to concentration variations in the standardisation sample is less than the repeatability of the spectrometer. In this situation, also information relating to well defined absorbance values may be obtained from the spectrum or spectra of the standardisation sample(s) for use in the standardisation of the spectrometer.

In essence the standardisation process comprises measuring in the spectrometer a single beam spectrum of the standardisation sample(s) ($SB_{SS}$) and a single beam spectrum of the zero-material ($SB_Z$); obtaining a dual beam spectrum which relates substantial only to the standardisation sample ($DB_{SS}$) by dividing, in the arithmetic unit associated with the spectrometer, the single beam spectra $SB_{SS}$ by $SB_Z$ at the same wavelengths; comparing in the arithmetic unit the frequency positions of the characteristic patterns of the standardisation sample(s) in the so obtained dual beam spectrum ($DB_{SS}$) with frequency positions previously defined as desired frequency positions; obtaining a mathematical transform $T_X$ from the comparison which describes a transition of the measured frequency positions to those of the desired frequency positions; and obtaining a mathematical transform $T_Y$ from a comparison in the arithmetic unit of measured ($DB_{SS}$) amplitude values from the standardisation sample(s) with previously defined desired amplitude values which transform $T_Y$ describes a transition of the measured values to those of the desired values. These transforms $T_X$, $T_Y$, as may be periodically updated in a new standardisation process, are then stored in the arithmetic unit for application thereby to all subsequently obtained spectral data of unknown samples being measured in the spectrometer in order to standardise these sample spectra.

In order to simplify the generation of one or both of the transforms $T_X$, $T_Y$, assumptions may be made as to the nature or the mathematical identity or type of the shift or transition required. Based on a knowledge of how the laser and the cuvette influences the acquired spectrum the complexity of the calculation and the number of variables required in order to describe the required translation may be reduced. Essentially then, the arithmetic unit need only calculate the set of variables to be used with the assumed transform function.

In known spectrometers this standardisation process is applied with a period much greater than the period between sample measurements and may be performed, for example, monthly. However, whilst the stability of the spectrometer in respect of frequency shift is sufficient that the associated transform ($T_X$) holds between successive performances of the standardisation process it has been observed that amplitude stability is often insufficient for the associated transform ($T_Y$) for amplitude values to hold between successive performances.

According to a first aspect of the present invention there is provided a method of compensating for amplitude drift in a spectrometer generating optical spectral data from an unknown sample, the method comprising:

performing a standardisation process including determining in an arithmetic unit associated with the spectrometer a mathematical transform from a comparison of acquired spectral amplitude data of a standardisation sample with previously defined desired spectral amplitude data, which transform describes a transition of the measured data to that of the desired data;

performing the standardisation process periodically throughout the lifetime of the spectrometer; and associated with a performance, preferably with each performance, of the standardisation process acquiring and storing in the spectrometer reference spectral amplitude data for a zero material and at least once acquiring in the spectrometer spectral amplitude data for the zero-material in an interval between successive performances of the standardisation process;

wherein the method further comprises the steps of, in the interval between successive performances:

modifying in the arithmetic unit the mathematical transform with a function dependent on the acquired reference spectral amplitude data and the at least once acquired spectral amplitude data associated with the zero material; and applying in the arithmetic unit the modified mathematical transform to acquired spectral amplitude data of an unknown sample.

In this manner standardised spectral data of an unknown sample may be obtained taking into account amplitude variations that occur more rapidly than the period between the performances of successive standardisation processes. Moreover, as it is current best practice to acquire zero material spectral data in the spectrometer more frequently than the performance of the standardisation processes, for example hourly and in some cases in intervals between the acquisitions in the spectrometer of spectral data from each new unknown sample, then no additional spectral measurements need be performed in the spectrometer.

Whereas the reference spectral amplitude data for a zero material will typically be acquired in the spectrometer for use in the arithmetic unit substantially at the same time as the dual beam spectrum which relates substantial only to the standardisation sample this is not essential. The reference spectral amplitude data for the zero material may be acquired in the spectrometer in a time interval after the generation of the spectrum of the standardisation sample during which time amplitude drift affecting measurements is unlikely to have occurred.

A presently preferred embodiment of the method according to the present invention will now be described in relation to the operation of a known FT interferometer based spectrometer. By way of example only, the spectrometer under consideration is configured to perform measurements on unknown liquid samples and is therefore equipped with a sample cuvette for holding the sample during the measurement. The exemplary spectrometer is adapted to generate spectra from the unknown liquid sample by transmitting radiation from the interferometer through the sample in the cuvette and onto a detector.

An arithmetic unit associated with the spectrometer according to the present embodiment is provided with access to digitized information representing a reference dual beam transmittance (or absorbance) spectrum of a standardisation liquid ($DB_{SSR}$) or at least representing information relating to the positions and amplitudes of characteristic absorptions of the liquid for use in the standardisation of the spectrometer, essentially in the manner described in U.S. Pat. No. 5,933,792 and outlined herein. This information may be provided from the spectrometer supplier or by the end-user making measurements on the standardisation liquid with the spectrometer and constitutes desired amplitude and usually also frequency related values towards which the output of the particular spectrometer will be standardised.

In the present example the standardisation liquid consists of water and propanol (3.83 w/w percent of propanol). This standardisation liquid is chosen as it has two well defined absorption peaks in a frequency range in which the present spectrometer is designed to perform measurements, here 1000-5000 cm$^{-1}$. These absorption peaks are easily identifiable in the transmittance (absorbance) spectrum of the standardisation liquid as two local minima (maxima) and since the concentration of propanol used is accurately and reproducibly known then so is the transmittance (absorbance) intensity values.

In order to perform a standardisation of the spectrometer at any time during its operational lifetime, the standardisation liquid is, at that time, introduced into the cuvette of the spectrometer in the same manner as an unknown sample and a measurement of the single beam transmittance spectrum $SB_{SS}$ of the standardisation liquid is performed and provided to the arithmetic unit. The standardisation liquid in the cuvette is then replaced with water, which acts as the zero material, and a similar single beam spectrum $SB_Z$ for water is also obtained into the arithmetic unit and both spectra processed in the unit to generate the dual beam transmittance (or absorbance) spectrum for the standardization liquid $DB_{SS}$.

This dual beam spectrum, $DB_{SS}$ is subsequently compared to the reference spectrum, $DB_{SSR}$ in order to obtain standardization parameters of mathematical transforms $T_X$, $T_Y$ respectively for the frequency position and amplitude corrections of subsequently obtained dual beam spectra, $DB_S$, of unknown samples.

Typically and as described in the present example, the actual standardization will take place on the basis of the absorbance (negative $\log_{10}$ of the transmittance) dual beam spectrum of the standardisation liquid, as it is intuitively more easily understandable to compare positions of absorption peaks than local minima in the spectra. In this manner, the local minima in the measured spectrum caused by absorption of propanol will be transformed into absorption peaks.

It is well understood that the differences between two spectra of the same sample measured at different times on the same instrument or by two different instruments will mainly be generated by a relatively few and well defined causes of which the most predominant are:
 a) a difference in sample cuvette thickness which will give a difference in the amount of light absorbed in the cuvette and sample,
 b) a difference in wavelength of the two lasers in the interferometers which will give a shift on the frequency axis of the final spectra, and
 c) a difference in the alignment of the IR light and the laser light in the interferometer will also give a shift on the frequency axis of the final spectra.

Considering the cause a), the difference may be caused by wear of the cuvette. In fact, cuvette materials such as $CaF_2$, which is a material typically employed in mid-IR measurements, are slightly hygroscopic, whereby the sample cuvette may actually be slightly dissolved during measurement of aqueous samples, such as milk samples. Whilst this process may only alter the path length through the sample holder by a few micrometers (μm) between successive performances of the standardisation process this becomes particularly significant for measurements made in the mid-IR spectral region where, due to relatively high absorption by samples in this region, path lengths through the sample tend to be of the order of a few tens of micrometers, typically between 30 μm to 50 μm.

According to Lambert-Beer's law, this difference will give a linear scaling of the absorbance axis of the measured spectrum.

Re. b), the Fourier transformation used in FT instruments requires that the interference signal produced in the interferometer and detected by the detector is scanned equidistantly as a function of the difference in light path, such as being the movement of a movable mirror. In typical FT instruments this is ensured by launching laser light into the interferometer and by triggering the measurements of the interference peak on, e.g., a phase lock of the laser light or on zero-crossings of the interfering laser light in the interferometer.

In this situation, a difference in laser light frequency will cause two different instruments to trigger the measurements of the interference pattern equidistantly at slightly different distances. Thus, this will give a difference on the frequency scale of the measured spectrum.

Due to the above, however, this difference will be a linear scaling of the frequency axis of the spectrum. As the Fourier transformed spectrum will be constituted of a number of equidistant points on the frequency axis, the distance of these points will be different from instrument to instrument. However, in order to correct this, the "ruler" constituted by the equidistant frequencies should merely be compressed or stretched. No non-linear effects will typically be generated in this process.

The same effect will be seen when other distance measuring means are used in this type of instrument. This is given by the Fourier transformation taking place.

Re. c), a frequency shift will be seen when the light in the interferometer does not follow exactly the same path as the laser light. In this situation the interference signal of the interfering light will be trigged equidistantly, such as on zero-crossings of the interfering laser light, but with a different distance compared to the situation where the laser light exactly overlaps the light. Thus, the "ruler" of the equidistant trigging will not be that of the laser wavelength but slightly shifted so that the above stretching or compressing of the "ruler" will still correct the frequency axis.

This adaption of the frequency axis may be performed on the basis of the identified positions of the two absorption peaks of the propanol in the standardisation liquid, when the positions of these peaks of the reference pattern are known.

A transform $T_X$ providing a linear scaling of the frequency axis may be employed in correcting the measured sample spectra $DB_S$. The frequency shift which will transfer any channel from the measured spectrum into the corresponding channel of the reference pattern may be described by a transform $T_X$ of the form: α·channel+β only two variables (α and β) are required in order to correct the frequency axis of future spectra in order to standardize this axis. In fact, as β is substantially zero, only α is required if a slightly smaller precision is sufficient. These factors α,β may be calculated from a consideration of a straight line plot through points constituted by, on the x axis the peak positions (channel number) and on the y axis the difference in channel number between the measured peak positions and those of the reference spectral data.

Performing this transform on the dual beam standardisation spectrum $DB_{SSt}$ measured at a time t, then the frequency axis of the shifted, measured spectrum $DB'_{SSt}$ will now coincide with that of the reference spectrum $DB_{SSR}$ and similarly transformed sample spectra $DB'_S$ will be standardised. As will be appreciated, such a frequency correction may also change the shape of the measured spectral peaks and so is preferably, but not essentially, performed before any transmittance (absorbance) axis correction is made.

In accordance with a) above, also the transmittance (absorbance) axis must be corrected. This correction may most simply be corrected on the basis of the transmittance difference between only a single channel of the standardisation spectra collected at time t and t=0, such as the transmittance difference in one of the identified peaks in the spectrum $DB_{SSt}$ and the reference pattern $DB_{SSR}$, and on the basis of the assumption that the correction is a linear correction (linear in absorbance being the $-\log_{10}$ of transmittance—see below) throughout the part of the spectrum which is interesting for the present purpose. Preferably this correction is performed using the already frequency corrected spectrum $DB'_{SSt}$. The only information of the reference pattern that is actually required is the channel numbers and transmittance values in which the two identified peaks of the (preferably) frequency corrected spectrum $DB'_{SSt}$ should be positioned when standardised. Thus, the reference pattern required for this standardisation is simply the peak points of the two peaks.

However, due to the interference of e.g. noise, it is often preferred to use a larger number of values in selected ranges in order to reduce the probability of error in the calculation.

Due to the above assumption that the correction of the absorbance axis will be a linear scaling in absorbance values, a transform $T_Y$ of the type: $b \cdot (DB'_{SSt})a$ may usefully be assumed.

As mentioned previously, in order to transform a transmittance spectrum into an absorbance spectrum, the negative logarithm should be taken of the transmittance spectrum. It is seen that this will give a linear correction of the absorbance axis of the spectrum, $\log_{10}(DB_{SSR})=a\cdot\log_{10}(DB'_{SSt})+\log_{10} b$ which means that a and $\log_{10}$ b may be found.

Thus, a and $\log_{10}$ b may be found by plotting, on one axis, the logarithm of the frequency shifted spectrum $DB'_{SSt}$ and, on the other axis, the logarithm of the reference spectrum $DB_{SSR}$. From this plot, which again results in a substantially straight line the best straight line through all points is found, using an ordinary Least Squares Fit, and the variables a and $\log_{10}$ b calculated. As, $\log_{10}$ b is close to zero and may be omitted if a less precise standardisation is sufficient.

Thus, from the above, the variables α, β, a and b may be found from a comparison of spectral data obtained from a standardisation sample during the lifetime of the spectrometer and equivalent data obtained as reference data. These variables will subsequently be stored for access by the arithmetic unit associated with the spectrometer for use within that unit to correct subsequent spectra of unknown samples in order to obtain standardised sample spectra.

The standardisation of a dual beam spectrum of an unknown sample ($DB_S$) will be performed in accordance with the above, where a frequency shifted spectrum $DB_S'$ will, preferably but not essentially, firstly be generated which will then be processed in the arithmetic unit using a transform of the type: $DB_{standardized}=b\cdot(DB'_S)^a$ in order to generate the standardised sample spectrum.

If the correction of the absorption axis was not a simple linear correction, there are multiple ways to standardise a spectrum. In the situation above, where a water absorption is positioned in the spectrum, and if this is also the situation in the spectra to be standardized, the transmittance correction may be performed for each "window" between the water absorptions. As these windows will be relatively small as compared to the full spectrum, the correction may with success be assumed to be linear in each window, whereby different a-values and b-values may be found for each window.

This method may give rise to non-continuities in the full spectrum if no water absorptions are present in this spectrum. This effect may be removed by, instead of the above, accepting that the correction is not homogeneous and instead determining individual a-values and b-values for each channel in the (preferably) frequency-corrected spectrum.

For example, for the point relating to the channel in question and e.g. the two nearest points on each side, an a-value and a b-value for this individual channel may be obtained.

Subsequently, two different polynomials may be fitted to the a-values and the b-values, respectively. These polynomials will then be used for the transmittance correction instead of the above global a-value and b-value.

A third method will be to simply fit a polynomial to the difference or ratio of the transmission of the frequency corrected spectrum of the standardisation material and the reference spectrum. This polynomial may thereafter be used to standardise the absorption axis of a spectrum.

According to the method of the present invention and as is known in the prior art, the above described standardisation procedure is performed periodically throughout the operational lifetime of the spectrometer. However amplitude drift which is essentially due to changes in the thickness of the sample cuvette occurs faster than the time interval between standardization events. The standardisation process according to the method of the present invention is adapted to accommodate this more rapid change.

In accordance with the present invention the change in path length ΔP through the cuvette of the spectrometer is a function F dependent on a reference single beam spectra of the zero material ($SB_{ZR}$), here obtained at the time of a preceding standardization event, and at a time between standardisation events ($SB_{Zt}$). This is described mathematically as $\Delta P=F(SB_{Zt}, SB_{ZR})$.

As discussed above the single beam spectrum of the zero material ($SB_Z$) is expected to contain information which is related to the spectrometer itself, independent of any sample material. In the present embodiment, where the zero material is water, the absorbance spectrum at different path lengths through the cuvette (i.e. cuvette thickness) is illustrated in FIG. 1 for path lengths from 26 μm to 96 μm inclusive in 10 μm steps. As can be seen, around the variable (channel number) 400 there is a good sensitivity to the path length change and the intensity value is essentially unchanged in the window around this variable.

The change in path length, ΔP, may be given as a constant multiplied by the absorbance. This may be calculated from a consideration of a straight line plot through points constituted by, on the x axis the absorbance at a fixed position (channel number) in the absorbance spectrum and on the y axis the path length at which the absorbance spectrum is obtained and the origin. In the present example it can be shown that ΔP=43·Absorbance, where Absorbance is given as $-\log_{10}(SB_{Zt}/SB_{ZR})$.

Amplitude values from more than one position may be employed to generate the relationship between measured amplitude and path length in order t improve accuracy and/or to account for sources of absorbance not associated with the zero liquid.

As will be appreciated from the foregoing the value $P_0 \cdot a_0$, where $P_0$ and $a_0$ are respectively the path length and the a-value obtained at the time of a standardisation, will be a constant k. As this holds true at all times then at a time, t, between standardisation events this constant may be given as $k=(P_0+\Delta P)\cdot a_t$, where $a_t$ is the a-value at time t and ΔP is the path length change since standardisation. Thus the a-value at time t may be given as $a_t=(P_0/(P_0+\Delta P))\cdot a_0$ and so according to the present invention the mathematical transform $T_Y$ may be modified with a factor of the form $(P_0/(P_0+\Delta P))$ in order to compensate for amplitude drift in intervals between standardisation events.

The value $P_0$ need not itself be measured but, as will be appreciated, may be calculated from the reference spectral data $DB_{SSR}$ and the spectral data $DB_{SSt}$ recorded by the spectrometer during a standardisation process. The value $P_0$ may be calculated as $P_0=(DB_{SSt}/DB_{SSR})\cdot P_R$, where $P_R$ is the path length associated with the generation of the reference spectral data. This path length $P_R$ may be provided as an element of the reference data which is made available to the arithmetic unit or may be readily calculated in the arithmetic unit using the reference spectral data.

The invention claimed is:
1. A method of compensating for amplitude drift in a spectrometer generating optical spectral data from an unknown sample in a sample holder, the method comprising:
 performing in the spectrometer a standardisation process including,
  measuring, in the spectrometer, a single beam spectrum of a standardization sample and a single beam amplitude spectrum of a zero material;

deriving, in an arithmetic unit associated with the spectrometer, a dual beam spectrum relating substantially only to the standardisation sample based on,
dividing, in the arithmetic unit, the single beam spectrum of the standardisation sample by the single beam amplitude spectrum of the zero material at common wavelengths; and
determining, in the arithmetic unit, a mathematical transform from a comparison of amplitude values of the derived dual beam spectrum relating substantially only to the standardization sample with previously defined desired spectral amplitude values, the mathematical transform describing a transition of the amplitude values of the derived dual beam spectrum relating substantially only to the standardization sample to the desired amplitude values, the mathematical transform including a factor having a first factor value that is calculated based on the comparison;
performing the standardisation process periodically throughout a lifetime of the spectrometer; acquiring, in the spectrometer, a single beam reference spectrum for a zero material associated with at least one performance of the standardization process;
acquiring a single beam spectrum for the zero material at least once in a time interval between performances of the standardisation process; and
between performances of the standardization process,
modifying, in the arithmetic unit, the mathematical transform with a function describing a change in optical path length through the sample holder, such that the factor of the mathematical transform is modified to have a value that is dependent on both the first factor value and the function describing the change in optical path length, the function describing the change in optical path length being dependent on the acquired single beam reference spectrum for the zero material and the spectrum for the zero material acquired at least once in the time interval between performances of the standardisation process;
generating, at the spectrometer, optical spectral data of an unknown sample in the sample holder; and
applying, in the arithmetic unit, the modified mathematical transform to the optical spectral data of the unknown sample generated by the spectrometer to generate amplitude drift-corrected optical spectral data of the unknown sample.

2. A method according to claim 1, wherein the function applied in the arithmetic unit to modify the mathematical transform comprises a function dependent on the ratio of single beam spectra of the zero material.

3. A method according to claim 1, wherein the reference spectral amplitude data is acquired in association with the performance of each standardisation.

4. A method according to claim 1, wherein the performances are successive performances of the standardisation process.

5. A spectrometric instrument comprising a spectrometer and an associated arithmetic unit for receiving spectral data from the spectrometer and processing the same to generate standardised spectral data wherein the arithmetic unit is programmed to operate to cause the spectral instrument to perform the method according to claim 1.

6. A spectrometric instrument as claimed in claim 5, wherein the spectrometer comprises a Fourier transform interferometer adapted to operate to acquire spectral data confined to the infra-red.

7. A spectrometric instrument as claimed in claim 6, wherein the spectral data is confined to the mid infra-red wavelength region.

* * * * *